United States Patent
Smith

(10) Patent No.: US 6,624,203 B1
(45) Date of Patent: Sep. 23, 2003

(54) NUCLEIC ACID BASES USED IN OPHTHALMIC SOLUTIONS

(76) Inventor: Francis X. Smith, 22 Fox Run La., Salem, NH (US) 03079

( * ) Notice: Subject to any disclaimer, the term of this patent is extended or adjusted under 35 U.S.C. 154(b) by 0 days.

(21) Appl. No.: 10/010,884

(22) Filed: Nov. 8, 2001

(51) Int. Cl.$^7$ .......................... A61K 47/32; A01N 43/04
(52) U.S. Cl. ..................... 514/772.4; 514/50; 514/46; 514/47; 514/48; 514/49; 514/45; 514/912; 424/78.04
(58) Field of Search ................. 514/772.4, 45, 514/616, 912, 50, 46, 47, 48, 49; 424/405, 429, 78.04

(56) References Cited

U.S. PATENT DOCUMENTS

| | | | |
|---|---|---|---|
| 4,136,175 A | * | 1/1979 | Rideout et al. ............... 514/48 |
| 4,136,534 A | | 1/1979 | Villa |
| 4,354,952 A | | 10/1982 | Riedhammer et al. |
| 4,361,548 A | | 11/1982 | Smith et al. |
| 4,525,346 A | | 6/1985 | Stark |
| 4,758,595 A | | 7/1988 | Ogunbiyi et al. |
| 4,783,488 A | | 11/1988 | Ogunbiyi et al. |
| 5,660,862 A | | 8/1997 | Park et al. |
| 5,674,450 A | | 10/1997 | Lin et al. |
| 5,719,110 A | | 2/1998 | Cook |
| 5,741,817 A | | 4/1998 | Chowhan et al. |
| 5,770,582 A | * | 6/1998 | von Borstel et al. .......... 514/45 |
| 5,780,450 A | | 7/1998 | Shade |
| 5,807,585 A | | 9/1998 | Martin et al. |
| 5,854,303 A | | 12/1998 | Powell et al. |
| 5,869,468 A | * | 2/1999 | Freeman ..................... 514/81 |
| 5,925,317 A | | 7/1999 | Rogalskyj et al. |
| 6,022,732 A | | 2/2000 | Bakhit et al. |
| 6,153,563 A | | 11/2000 | Smith et al. |
| 6,309,596 B1 | | 10/2001 | Xia et al. |
| 6,309,658 B1 | | 10/2001 | Xia et al. |

* cited by examiner

Primary Examiner—James M. Spear
Assistant Examiner—Blessing Fubara
(74) Attorney, Agent, or Firm—Jaeckle Flesichmann & Mugel, LLP

(57) ABSTRACT

An ophthalmic solutions that are broad ranged and effective in low concentrations relative to state of the art systems. In particular it has been found that ophthalmic solutions comprising 0.00001 to about 1.0 percent by weight of a nucleotide, a nucleoside or a purine or pyrimidine base; 0.00001 to about 0.05 percent by weight a cationic, polymeric preservative display an effective preservative capacity, and an increased capacity over state-of-the-art preservative systems.

6 Claims, No Drawings

NUCLEIC ACID BASES USED IN OPHTHALMIC SOLUTIONS

FIELD OF THE INVENTION

This invention relates to ophthalmic solutions used to treat eyes, to deliver active pharmaceutical agents to eyes and to treat ophthalmic devices that in use directly contact corneal tissues. Ophthalmic solutions are used to regularly treat and condition eyes and articles and devices that are regularly used in eyes, such as contact lenses. Because of the intimate contact that such solutions have with corneal tissue, several problems or concerns are regularly presented. For instance, for solutions directly in contact with corneal tissue the compatibility of the solution with the tissue, its ability to not damage or irritate, is important. This compatibility issue is also important for solutions used to treat devices that contact corneal tissue, such as contact lenses and the like. Furthermore, prolonged contact with corneal tissue can lead to the accumulation of material on corneal tissue, or on devices in contact with the solution that then leads to adverse reactions.

Preservative efficacy is measured by the amount that a solution decreases the viability of bacterial or fungal populations. In general, there is an expected trade-off between preservative efficacy and corneal tissue compatibility, as well as "comfort." Furthermore, the field of the invention relates to preservative systems that are broad ranged, and effective against not only bacterial, but also fungal sources of infection.

International Patent Publication No. WO 91/01763 discloses that solutions having very low concentrations of peroxide, i.e., from 0.01 to 0.5 percent more preferably 0.05 to 0.2 percent can provide disinfection without requiring neutralization. Use of the present invention greatly enhances the microbicidal efficacy of peroxide in such low concentrations.

U.S. Pat. No. 4,758,595 (Ogunbiyi, et al.) discloses that polyhexamethylene biguanide (PHMB) and its water-soluble salts can fulfill minimal disinfection and be harmless to the eye and the lens, if used with a specific buffer, a surfactant, and in specific concentrations.

U.S. Pat. No. 5,869,468 teaches methods for treatment of conditions of abnormally increased intraocular pressure, particularly those caused by glaucoma, by administration of phosphonylmethoxyalkyl nucleoside analogs are provided. The compositions formulated and packaged for intraocular administration for use in the methods are also provided. Administration of the compound may be by intravitreal injection, aqueous humor injection, injection into the external layers of the eye, such as subconjunctival injection or subtenon injection, or may be, when penetrating derivatives are used, by topical application to the eye. The degree of reduction in pressure is dosage-dependent, and significant reduction in pressure is obtained. A single injection can produce prolonged, and perhaps permanent, lowering of the intraocular pressure. Typical formulations have between about 0.50 ml and 0.150 ml and comprises a concentration of the compound of about 10 mu g/0.100 ml up to about 100 mu g/0.100 ml U.S. Pat. No. 5,770,582 relates to compositions comprising 2'-deoxyribonucleosides. The invention also relates to methods of accelerating the healing of wounds, abrasions, cuts, incisions, and superficial burns induced by heat, sunlight, chemical agents, or infections, and methods for ameliorating the effects of aging of the epidermal tissues comprising administering the compositions of the present invention to an animal. More particularly, it has been found that the combination of 2'-deoxyribonucleosides, 2'-deoxycytidine and 2'-deoxyguanosine, produces a substantial increase in the rate of healing of experimental wounds compared to controls and other two-way combinations. The compositions may contain (a) a major amount of 2'-deoxycytidine and an effective amount of 2'-deoxyguanosine, or, (b) a major amount of 2'-deoxyguanosine and an effective amount of 2'-deoxycytidine. Desirably the binary composition contains from 10% to 90% (by mole) 2'-deoxycytidine and 90% to 10% 2'-deoxyguanosine. Preferred compositions contain from 25% to 75% of the two components. This method teaches very concentrated forms of specific nucleosides in topical form, and does not suggest any antimicrobial function.

U.S. Pat. No. 4,136,175 provides that nucleotide derivatives of certain 2,6 substituted purines have been discovered to have anti-viral activity. Novel compounds and their pharmaceutically acceptable salts, pharmaceutical formulations containing the compounds of this invention, and the treatment of viral infections with these formulations are all disclosed. 2,6 Diamino-9-(beta-D arabinofuranosyl)-purine-5'-phosphate is an example of a more active compound of this invention. There is no suggestion that un-modified nucleotides have the same anti-viral properties.

SUMMARY OF THE INVENTION

The present invention relates to ophthalmic solutions that are broad ranged and effective in low concentrations relative to state of the art systems. In particular it has been found that ophthalmic solutions comprising 0.00001 to about 1.0 percent buy weight of a nucleotide, a nucleoside or a purine or pyrimidine base; 0.00001 to about 0.05 percent by weight a cationic, polymeric preservative display an effective preservative capacity, and an increased capacity over state-of-the-art preservative systems.

The invention also relates to articles of manufacture that employ the solution in their operation. For instance, vials employed to store contact lenses for sale may be filled using the solution

DETAILED DESCRIPTION OF THE INVENTION

The present invention relates to ophthalmic solutions that are broad ranged and effective in low concentrations relative to state of the art systems. In particular it has been found that ophthalmic solutions comprising 0.00001 to about 1.0 percent buy weight of a nucleotide, a nucleoside or a purine or pyrimidine base and 0.00001 to about 0.05 percent by weight a cationic, polymeric preservative display an effective preservative capacity, and an increased capacity over state-of-the-art preservative systems.

The purine and pyrimidine bases used in the present invention (e.g. adenine, guanine, uracil, cytosine and thymine) are well known building blocks of nucleic acid chemistry. As are the nucleosides which consist of a purine or pyrimidine base linked to a pentose (e.g. Ribonucleoside—adenosine, guanosine, uridine, cytidine and Deoxyribonucleoside—deoxyadenosine, deoxyguanosine, deoxythymidine, deoxycytidine). The nucleotides, of course, are the phosphate esters of the nucleosides (Ribonucleotide—adenylate (AMP, ADP, ATP), guanylate (GMP, GDP, GTP), uridylate (UMP, UDP, UTP), cytidylate (CMP, CDP, CTP), Deoxyadenylate (dAMP, dADP, dATP), deoxyguanylate (dGMP, dGDP, dGTP), deoxythymidylate (dUMP, dUDP, dUTP), deoxycytidylate (dCMP, dCDP, dCTP). Collectively, these are termed nucleic acid bases.

The cationic polymeric preservative includes polymeric biguanides such as polymeric hexamethylene biguanides (PHMB), and combinations thereof. Such cationic polymeric biguanides, and water-soluble salts thereof, having the following formula:

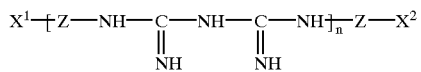

wherein Z is an organic divalent bridging group which may be the same or different throughout the polymer, n is on average at least 3, preferably on average 5 to 20, and $X^1$ and $X^2$ are

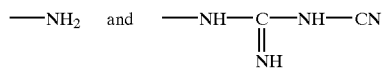

One preferred group of water-soluble polymeric biguanides will have number average molecular weights of at least 1,000 and more preferably will have number average molecular weights from 1,000 to 50,000. Suitable water-soluble salts of the free bases include, but are not limited to hydrochloride, borate, acetate, gluconate, sulfonate, tartrate and citrate salts.

The above-disclosed biguanides and methods of preparation are described in the literature. For example, U.S. Pat. No. 3,428,576 describes the preparation of polymeric biguanides from a diamine and salts thereof and a diamine salt of dicyanimide.

Most preferred are the polymeric hexamethylene biguanides, commercially available, for example, as the hydrochloride salt from Zeneca (Wilmington, Del.) under the trademark Cosmocil™ CQ. Such polymers and water-soluble salts are referred to as polyhexamethylene (PHMB) or polyaminoptopyl biguanide (PAPB). The term polyhexamethylene biguanide, as used herein, is meant to encompass one or more biguanides have the following formula:

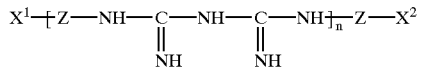

wherein Z, $X^1$ and $X^2$ are as defined above and n is from 1 to 500.

Depending on the manner in which the biguanides are prepared, the predominant compound falling within the above formula may have different $X^1$ and $X^2$ groups or the same groups, with lesser amounts of other compounds within the formula. Such compounds are known and are disclosed in U.S. Pat. No. 4,758,595 and British Patent 1,432,345, which patents are hereby incorporated. Preferably, the water-soluble salts are compounds where n has an average value of 2 to 15, most preferably 3 to 12.

In another embodiment, a polymeric biguanide is used in combination with a bis(biguanide) compound. Polymeric biguanides, in combination with bisbiguanides such as alexidine, are effective in concentrations as low as 0.00001 weight percent (0.1 ppm). It has also been found that the bactericidal activity of the solutions may be enhanced or the spectrum of activity broadened through the use of a combination of such polymeric biguanides with alexidine or similar biguanides.

An optional non-biguanide disinfectant/germicide can be employed as a solution preservative, but it may also function to potentiate, complement or broaden the spectrum of microbiocidal activity of another germicide. This includes microbiocidally effective amounts of germicides which are compatible with and do not precipitate in the solution, in concentrations ranging from about 0.00001 to about 0.5 weight percent, and more preferably, from about 0.0001 to about 0.1 weight percent. Suitable complementary germicidal agents include, but are not limited to, quaternary ammonium compounds or polymers, thimerosal or other phenylmercuric salts, sorbic acid, alkyl triethanolamines, and mixtures thereof. Representative examples of the quaternary ammonium compounds are compositions comprised of benzalkonium halides or, for example, balanced mixtures of n-alkyl dimethyl benzyl ammonium chlorides. Other examples include polymeric quaternary ammonium salts used in ophthalmic applications such as poly [(dimethyliminio)-2-butene-1,4-diyl chloride], [4-tris(2-hydroxyethyl)ammonio]-2-butenyl-w-[tris(2-hydroxyethy) ammonio]dichloride (chemical registry number 75345-27-6) generally available as polyquatemium 1 (r) from ONYX Corporation, or those described in U.S. Pat. No. 6,153,568.

The acid-addition salts of the germicides used in the present composition may be derived from an inorganic or organic acid. In most circumstances it is preferable that the salts be derived from an acid which is readily water soluble and which affords an anion which is suitable for human usage, for example a pharmaceutically-acceptable anion. Examples of such acids are hydrochloric, hydrobromic, phosphoric, sulphuric, acetic, D-gluconic, 2-pyrrolidino-5-carboxylic, methanesulphonic, carbonic, lactic and glutamic acids.

Peroxide sources may also be included in the formulations of the present invention and are exemplified by hydrogen peroxide, and such compounds, which provide an effective resultant amount of hydrogen peroxide, such as sodium perborate decahydrate, sodium peroxide, urea peroxide and peracetic acid, an organic peroxy compound.

The pH of the present solutions should be maintained within the range of 5.0 to 8.0, more preferably about 6.0 to 8.0, most preferably about 6.5 to 7.8. Suitable buffers may be added, such as boric acid, sodium borate, potassium citrate, citric acid, sodium bicarbonate, TRIS, bis-tris-propane and various mixed phosphate buffers (including combinations of $Na_2HPO_4$, $NaH_2PO_4$ and $KH_2PO_4$) and mixtures thereof.

Borate buffers enhance the efficacy of PAPB. Generally, buffers will be used in amounts ranging from about 0.05 to 2.5 percent by weight, and preferably, from 0.1 to 1.5 percent.

The solutions of the present invention may further contain other additives including but not limited to buffers, tonicity agents, demulcents, wetting agents, preservatives, sequestering agents (chelating agents), surface active agents, and enzymes.

Ophthalmologically acceptable chelating agents useful in the present invention include amino carboxylic acid compounds or water-soluble salts thereof, including ethylenediaminetetraacetic acid, nitrilotriacetic acid, diethylenetriamine pentaacetic acid, hydroxyethylethylenediaminetriacetic acid, 1,2-diaminocyclohexanetetraacetic acid, ethylene glycol bis (beta-aminoethyl ether) in N, N, N', N' tetraacetic acid (EGTA), aminodiacetic acid and hydroxyethylamino diacetic acid. These acids can be used in the form of their water soluble salts, particularly their alkali metal salts. Especially preferred chelating agents are the di-, tn- and tetra-sodium salts of ethylenediaminetetraacetic acid (EDTA), most preferably disodium EDTA (Disodium Edetate).

Other chelating agents such as citrates and polyphosphates can also be used in the present invention. The citrates which can be used in the present invention include citric acid and its mono-, di-, and tri-alkaline metal salts. The polyphosphates which can be used include pyrophosphates, triphosphates, tetraphosphates, trimetaphosphates, tetrametaphosphates, as well as more highly condensed phosphates in the form of the neutral or acidic alkali metal salts such as the sodium and potassium salts as well as the ammonium salt.

The solutions of the invention are compatible with both rigid gas permeable and hydrophilic contact lenses and other ophthalmic devices and instruments during storage, cleaning, wetting, soaking, rinsing and disinfection.

A typical aqueous solution of the present invention may contain additional ingredients which would not affect the basic and novel characteristics of the active ingredients described earlier, such as tonicity agents, surfactants and viscosity inducing agents, which may aid in either the lens cleaning or in providing lubrication to the eye. Suitable tonicity agents include sodium chloride, potassium chloride, glycerol or mixtures thereof The tonicity of the solution is typically adjusted to approximately 240–310 milliosmoles per kilogram solution (mOsm/kg) to render the solution compatible with ocular tissue and with hydrophilic contact lenses. In one embodiment, the solution contains 0.01 to 0.35 weight percent sodium chloride.

The solutions employed in the present invention may also include surfactants such as a polyoxyethylene-polyoxypropylene nonionic surfactant which, for example, can be selected from the group of commercially available surfactants having the name poloxamine or poloxamer, as adopted by The CTFA International Cosmetic Ingredient Dictionary. The poloxamine surfactants consist of a poly(oxypropylene)-poly(oxyethylene) adduct of ethylene diamine having a molecular weight from about 7,500 to about 27,000 wherein at least 40 weight percent of said adduct is poly(oxyethylene), has been found to be particularly advantageous for use in conditioning contact lenses when used in amounts from about 0.01 to about 15 weight percent. Such surfactants are available from BASF Wyandotte Corp., Wyandotte, Mich., under the registered trademark "Tetronic". The poloxamers are an analogous series of surfactants and are polyoxyethylene, polyoxypropylene block polymers available from BASF Wyandotte Corp., Parsippany, N.J. 07054 under the trademark "Pluronic".

The HLB of a surfactant is known to be a factor in determining the emulsification characteristics of a nonionic surfactant. In general, surfactants with lower HLB values are more lipophilic, while surfactants with higher HLB values are more hydrophilic. The HLB values of various poloxamines and poloxamers are provided by BASF Wyandotte Corp., Wyandotte, Mich. Preferably, the HLB of the surfactant in the present invention is at least 18, more preferably 18 to 32, based on values reported by BASF.

Additional compatible surfactants that are known to be useful in contact wetting or rewetting solutions can be used in the solutions of this invention. The surfactant should be soluble in the lens care solution and non-irritating to eye tissues. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples of the preferred class include polysorbate 20 (available from ICI Americas Inc., Wilmington, Del. 19897 under the trademark Tween® 20), polyoxyethylene (23) lauryl ether (Brij® 35), polyoxyethylene (40) stearate (Myrj® 52), polyoxyethylene (25) propylene glycol stearate (Atlas® G 2612). Brij® 35, Myrj® 52 and Atlas® G 2612 are trademarks of, and are commercially available from, ICI Americas Inc., Wilmington, Del. 19897.

Various other surfactants suitable for in the invention can be readily ascertained, in view of the foregoing description, from McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C. however, the preferred surfactants are commercially available surfactants sold under the trademark Cremaphor RH40® by BASF which are polyoxyethoxylated castor oils.

Suitable viscosity inducing agents can include lecithin or the cellulose derivatives such as hydroxymethylcellulose, hydroxypropylcellulose and methylcellulose in amounts similar to those for surfactants, above.

SPECIFIC EMBODIMENT OF THE PRESENT INVENTION AND COMPARISON WITH STATE-OF-THE-ART SOLUTIONS

EXAMPLE 1

Antimicrobial Activity

A formulation containing guanine was prepared in a 0.2% phosphate buffer. The solution was made isotonic with sodium chloride and preserved with polyhexamethylene biquanide at 0.0001%. The pH was adjusted to 7.2 with either 1 N sodium hydroxide or 1 N hydrochloric acid. The in vitro microbicidal activity of the test and control solution was determined by exposing C. albicans to 10 ml of each solution at room temperature for 4 and 24 hours. Subsequently, an aliquot of each solution was serial diluted onto agar plates and incubated for 48 hours at elevated temperatures. At the conclusion of the incubation period the plates are examined for the development of colonies. The log reduction was determined based on a comparison to the inoculum control. The following table provides the results of the in vitro studies.

| Additive | 4 hours | 24 hours |
| --- | --- | --- |
| Guanine | 0.97 | 3.05 |
| $PO_4$ Control | 1.03 | 2.40 |

EXAMPLE 2

Acanthamoeba Data

A formulation containing 0.5% guanine was prepared in a 0.2% glycine buffer at pH 7.35. The solution was preserved with polyhexamethylene biquanide at 0.02%. A similar control was prepared except without the guanine. The in vitro anti-acanthamoeba activity of the test and control solutions was determined by exposing Acanthamoeba castellanii cysts to 2 ml of each solution at room temperature for 10 minutes. Subsequently, an aliquot of each solution was serial diluted in duplicate and incubated for 14 days. At the conclusion of the incubation period, the dilutions were examined for viable Acanthamoeba trophozoites. The log reduction was determined based on a comparison to the inoculum control. A negative control was performed to verify the technique. The following table provides the results of the in vitro studies.

| Formulation | 0 dilution | −1 dilution | −2 dilution | −3 dilution | −4 dilution | −5 dilution | Log Reduction |
|---|---|---|---|---|---|---|---|
| Guanine in glycine buffer | Growth | No Growth Growth | No Growth No Growth | No Growth No Growth | No Growth No Growth | No Growth No Growth | 3.0 |
| Glycine buffer control | Growth | Growth Growth | No Growth No Growth | No Growth No Growth | No Growth No Growth | No Growth No Growth | 2.0 |
| Positive control | Growth | Growth Growth | Growth Growth | Growth Growth | No Growth No Growth | No Growth No Growth | NA |
| Negative control | No Growth | No Growth No Growth | No Growth No Growth | No Growth No Growth | No Growth No Growth | No Growth No Growth | NA |

The results of this test indicated that guanine improves the activity of preserved formulations against Acanthamoeba.

What is claimed is:

1. An ophthalmic solution for delivery of an active pharmaceutical agent to corneal tissue comprising:

0.00001 to about 1.0 percent by weight of a nucleic acid base;

0.00001 to about 0.05 percent by weight a cationic, polymeric preservative;

sufficient amount of a buffer agent which provides said solution with a pH between 6.5 and 7.5;

an effective amount of a pharmaceutical agent.

2. A contact lens treatment solution 0.00001 to about 1.0 percent by weight of a nucleic acid base;

0.0001 to about 0.05 percent by weight a cationic, polymeric preservative; and sufficient amount of a buffer agent which provides said solution with a pH between 6.5 and 7.5.

3. A contact lens cleaning solution comprising 0.00001 to about 1.0 percent by weight of a nucleic acid base;

0.01 to about 2 percent by weight of a state of the art ophthalmic surfactant.

4. The contact lens cleaning solution of claim 3 wherein said surfactant is chosen from the group consisting of:

polyoxyethylene-polyoxypropylene nonionic surfactants;

poly(oxypropylene)-poly(oxyethylene) adducts of ethylene diamine having a molecular weight from about 7,500 to about 27,000 wherein at least 40 weight percent of said adduct is poly(oxyethylene), polyoxyethylene: polyoxypropylene block polymers and polyoxyethoxylated castor oils.

5. A contact lens vial storage apparatus comprising an aqueous solution containing 0.00001 to about 1.0 percent by weight of a nucleic acid base and 0.00001 to 0.001 percent by weight of a preservative agent;

a contact lens immersed in said solution; and a storage container for said aqueous solution and said contact lens.

6. An ophthalmic solution for treating irritated corneal tissue comprising:

0.00001 to about 1.0 percent by weight of a nucleic acid base;

sufficient amount of a buffer agent which provides said solution with a pH between 6.5 and 7.5;

0.001 to about 2 percent of a surfactant a.

* * * * *